United States Patent
Melloni et al.

(10) Patent No.: US 6,984,739 B2
(45) Date of Patent: Jan. 10, 2006

(54) PROCESS FOR PREPARING R-(-)-CARNITIN FROM S-(-)-CHLOROSUCCINIC ACID OR FROM A DERIVATIVE THEREOF

(75) Inventors: Piero Melloni, Bresso (IT); Alberto Cerri, Gessate (IT); Marco Santagostino, Magenta (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/716,453

(22) Filed: Nov. 20, 2003

(65) Prior Publication Data

US 2004/0102645 A1    May 27, 2004

Related U.S. Application Data

(62) Division of application No. 09/959,717, filed as application No. PCT/IT00/00187 on May 12, 2000, now Pat. No. 6,677,476.

(30) Foreign Application Priority Data

| May 18, 1999 | (IT) | ......................... RM99A000310 |
| Oct. 29, 1999 | (IT) | ......................... RM99A000670 |
| Feb. 10, 2000 | (IT) | ..................... RM2000A000061 |

(51) Int. Cl.
  *C07D 307/34*  (2006.01)
  *C07C 229/00*  (2006.01)
  *C07C 55/02*  (2006.01)
(52) U.S. Cl. ....................... 549/254; 562/568; 562/596
(58) Field of Classification Search ................ 549/254; 562/568, 596
  See application file for complete search history.

(56) References Cited

U.S. PATENT DOCUMENTS 4,143,070 A    3/1979  Walker ....................... 606/230
4,265,247 A    5/1981  Lenz ........................... 606/323
5,473,104 A    12/1995  McCarthy .................... 562/567

FOREIGN PATENT DOCUMENTS

| DE | 31 44 698 | 5/1983 |
| WO | WO 99 05092 A | 2/1999 |

OTHER PUBLICATIONS

Dymicky, Preparation of monomethyl furnarate, 1983, 15(4), 233-8, abstract p. 1.*
Arnold et al, Synthesis of Stereoregular Poly(alkyl malolactonates), Makromolekulare Chemi, Macromolecular Symposia, No. 6, 1986, pp. 285-303.
Frick et al, "An Efficient Synthesis of Enantiomerically Pure (R)-(2-Benzyloxyethyl) oxirane from (S)-Aspartic Acid", No. 7, Jul. 1992, pp. 621-623.
Merck Index, Tenth Edition, 1983, Merck & Co., Inc., New Jersey, pp. 1377 and 2073.

* cited by examiner

*Primary Examiner*—Cecilia J. Tsang
*Assistant Examiner*—Taylor Victor Oh
(74) *Attorney, Agent, or Firm*—Nixon & Vanderhye P.C.

(57) ABSTRACT

An inner salt of L-carnitine is prepared by reduction, with a suitable reducing agent, of a compound of formula (I):

$$X_1CO\diagdown\underset{Y}{\overset{}{\diagup}}\diagdown COX_2 \quad (1)$$

where $X_1$ and $X_2$, which may be the same or different, are hydroxy, $C_1$–$C_4$ alkoxy, phenoxy, halogen, or $X_1$ and $X_2$, when taken together are an oxygen atom and the resulting compound is a derivative of succinic anhydride; Y is halogen, a mesyloxy or a tosyloxy group, and subsequent treatment with water, then with a base and then with trimethylamine.

1 Claim, No Drawings

PROCESS FOR PREPARING R-(−)-CARNITIN FROM S-(−)-CHLOROSUCCINIC ACID OR FROM A DERIVATIVE THEREOF

CROSS-REFERENCE TO RELATED APPLICATION

This application is a divisional of application Ser. No. 09/959,717 filed Nov. 6, 2001 (allowed Sep. 3, 2003), now U.S. Pat. No. 6,677,476, which is a U.S. national phase of PCT/IT00/00187 filed May 12, 2000.

The invention described herein relates to a process for the preparation of R-(−)-carnitine (L-(−)-carnitine or R-(−)-3-hydroxy-4-(trimethylammonium)butyrate), hereinafter referred to, for the sake of brevity, as L-carnitine, starting from S-(−)-chlorosuccinic acid or one of its derivatives.

BACKGROUND TO THE INVENTION

As is known, carnitine possesses an asymmetrical carbon atom and the enantiomer L-carnitine is the isomer present in living organisms, where it is essential for fatty acid metabolism and functions actively in the transport of fatty acids across the mitochondrial membranes. For this reason L-carnitine, in addition to being a life-saving drug for those who suffer from an L-carnitine deficiency of genetic origin and to being used in cases of temporary L-carnitine deficiency, such as, for instance, those occurring after haemodialysis (U.S. Pat. No. 4,272,549, Sigma-Tau), plays an important role in energy metabolism and is regarded as a non-toxic natural product capable of enhancing cardiac function. It is therefore used as a support drug in the treatment of various heart diseases such as ischaemia, angina pectoris, arrhythmias, etc. (U.S. Pat. No. 4,649,159 and U.S. Pat. No. 4,656,191 Sigma-Tau). L-carnitine and its derivatives, moreover, have also been used to a significant extent as serum lipid lowering agents, anticonvulsants and blood product preservatives. Recently, one of its derivatives, propionyl L-carnitine (Dromos®), was launched on the Italian market for the treatment of intermittent claudication (U.S. Pat. No. 4,968,719, EP 0793962, Sigma-Tau).

There is also a substantially growing use of L-carnitine as a food supplement in the field of the so-called 'health foods' or "nutraceuticals".

All this explains why L-carnitine is produced industrially in large amounts and also why several attempts have been made to improve the industrial synthesis of L-carnitine in terms of the cost of the product.

From a general point of view, the synthesis pathways that can be used to synthesise L-carnitine are essentially three.

The first of these, starting from non-chiral or racemic compounds, passes through racemic intermediates, at the level of one of which the separation of the useful enantiomer occurs, with methods known to experts in pharmaceutical technology. Though this synthesis pathway presents the advantage of being able to rely on starting materials with a relatively low cost, for example, racemic carnitinamide (U.S. Pat. No. 4,254,053, Sigma-Tau); racemic 2,3-dichloro-1-propanol (N. Kasai and K. Sakaguchi, Tetrahedron Lett. 1992, 33, 1211); 3-butenoic acid (D. Bianchi, W. Cabri, P. Cesti, F. Francalanci, M. Ricci, J. Org. Chem., 1988, 53, 104); racemic 3-chloro-2-hydroxy-trimethylammonium chloride (R. Voeffray, J. C. Perlberger, L. Tenud and J. Gosteli, Helv. Chim. Acta, 1987, 70, 2058); racemic epichlorohydrin (H. Löster and D. M. Müller, Wiss. Z. Karl-Marx-Univ. Leipzig Math.-Naturwiss. R. 1985, 34, 212); diketene (L. Tenud, Lonza, DE 2,542,196, 2,542,227 and DE 2,518, 813), it also presents a serious drawback, in that, at the moment one wishes to isolate the useful enantiomer from a racemic mixture, there is a theoretical loss of at least 50% of the product on which said separation is operated. In practice, then, the yields in this synthesis step are substantially lower (U.S. Pat. No. 4,254,053, Sigma-Tau) and there is the drawback of having to recover the chiral compound used for the separation of the racemic mixture.

The second synthesis pathway, again starting from non-chiral products, "creates" the chiral centre of the configuration desired, operating a synthesis step in a chiral environment, whether by means of a catalyst (H. C. Kolb, Y. L. Bennani and K. B. Sharpless, Tetrahedron: Asymmetry, 1993, 4, 133; H. Takeda, S. Hosokawa, M. Aburatani and K. Achiwa, Synlett, 1991, 193; M. Kitamura, T. Ohkuma, H. Takaya and R. Noyori, Tetrahedron Lett., 1988, 29, 1555), or by means of an enzyme (U.S. Pat. No. 4,707,936, Lonza). The disadvantages of this pathway are the high cost of the catalysts and the fact that, at the time the chiral centre is created catalytically, one is normally unable to obtain the pure enantiomer, but mixtures are obtained with variable enantiomeric excesses of the useful isomer, with all the consequent difficulties of having to separate two substances with the same physico-chemical characteristics. In the case of the use of micro-organisms in continuous-cycle reactors, the transformation of the starting products into end products is never complete and the end product has to be scrupulously purified of all organic impurities of cellular origin, which are dangerous in that they are potential allergens.

The third synthesis pathway involves the use of a chiral starting product, which is transformed into L-carnitine via a series of reactions which, if the chiral centre is affected, must be stereospecific, which means that the stereochemistry of said centre must be maintained or completely inverted during the reaction, which is not always easy to achieve. If, on the other hand, the synthesis step does not affect the chiral centre, the enantiomeric excess (ee) of the end product must be the same, or very close to, the starting product, which means that "racemising" reaction conditions must be carefully avoided. Another limitation is the cost of the chiral starting products, which is normally much higher than that of non-chiral products. The effect of these difficulties has been that none of the various processes starting from chiral products such as, for example, la R-(−)-epichlorohydrin (M. M. Kabat, A. R. Daniewski and W. Burger, Tetrahedron: Asymmetry, 1997, 8, 2663); D-galactono-1,4-lactone (M. Bols, I. Lundt and C. Pedersen, Tetrahedron, 1992, 48, 319); R-(−)-malic acid (F. B. Bellamy, M. Bondoux, P. Dodey, Tetrahedron Lett. 1990, 31, 7323); R-(+)-4-chloro-3-hydroxybutyric acid (C. H. Wong, D. G. Drueckhammer and N. M. Sweers, J. Am. Chem. Soc., 1985, 107, 4028; D. Seebach, F. Giovannini and B. Lamatsch, Helv. Chim. Acta, 1985, 68, 958; E. Santaniello, R. Casati and F. Milani, J. Chem. Res., Synop., 1984, 132; B. Zhou, A. S. Gopalan, F. V. Middlesworth, W. R. Shieh and C. H. Sih; J. Am. Chem. Soc., 1983, 105, 5925); 4-hydroxy-L-proline (P. Renaud and D. Seebach, Synthesis, 1986, 424); (−)-β-pinene (R. Pellegata, I. Dosi, M. Villa, G. Lesma and G. Palmisano, Tetrahedron, 1985, 41, 5607); L-ascorbic acid or arabinose (K. Bock, I. Lundt and C. Pederson; Acta Chem. Scand., Ser. B, 1983, 37, 341); D-mannitol (M. Fiorini and C. Valentini, Anic, EP 60.595), has to date been used for the industrial production of L-carnitine.

A case apart is the Sigma Tau Italian patent No. 1,256, 705, which may be regarded as a mixture of the first and second synthesis pathways. What it describes, in fact, is the preparation of L-carnitine starting from D-(+)-carnitine, obtained as a discard product from the L-carnitine preparation process by resolution of the carnitinamide racemic mixture by means of camphoric acid (U.S. Pat. No. 4,254, 053, Sigma-Tau).

The bibliographical and patent references cited above merely give some idea of the vast body of work carried out in order to find an economically advantageous synthesis of L-carnitine. The fact is that the only two processes which have proved industrially and economically valid are those used by the two main manufacturers of L-carnitine, Sigma-Tau and Lonza, as described in the two above-mentioned patents, U.S. Pat. No. 4,254,053 and U.S. Pat. No. 4,708, 936, which date back to 1978 and 1987, respectively.

SUMMARY OF THE INVENTION

A process has now been found which starts from a chiral product and solves all the problems of the "third pathway", that is to say the problem of the cost of the starting product and those of the stereospecificity and regiospecificity of the reactions necessary in order to pass from S-(−)-chlorosuccminc acid, or one of its derivatives, to L-carnitine. The L-carnitine obtained is, in fact, particularly pure, with a D-carnitine percentage ≦0.2%.

In particular, the invention described herein relates to a process for the preparation of L-carnitine inner salt which includes the reduction, with a suitable reducing agent, of a compound of formula (I)

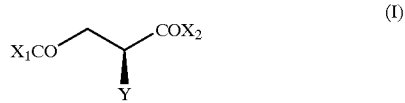

(I)

where:

$X_1$ and $X_2$, which may be the same or different, are hydroxy, $C_1$–$C_4$ alkoxy, phenoxy, halogen; or $X_1$ and $X_2$, when taken together are an oxygen atom and the resulting compound is a derivative of succinic anhydride;

Y is halogen, the mesyloxy or the tosyloxy group;

and subsequent treatment with a base and then with trimethylamine.

Examples of $C_1$–$C_4$ alkoxy groups are methoxy, ethoxy, propoxy, isopropoxy, butoxy, isobutoxy and ter-butoxy. The methoxy and ethoxy groups are preferred. Examples of halogen are chlorine, bromine and iodine. Chlorine is preferred.

The reduction of the compound of formula (I) is done with a suitable reducing agent, which may be selected from those available by those having ordinary experience in the field on the basis of their own general knowledge of the sector. Reducing agents suitable for implementing the process according to the invention described herein are hydrides. Examples of hydrides are diborane, mixed hydrides such as lithium and aluminimum hydride, lithium or sodium borohydride. The choice of a suitable reducing agent will be made in relation to the compound of formula (I) to be treated. This choice is made by the person having ordinary experience in the field on the basis of his or her general knowledge and no further explanation is necessary.

The process according to the invention is carried out in a suitable reaction medium, such as an organic solvent, preferably aprotic, for example, tetrahydrofuran (THF), dioxane, ethylene glycol dimethyl ether (DME) or 2-methoxyethyl ether (Diglime).

The reaction temperature, reactant concentrations and all other parameters useful for determining the reaction conditions can be obtained by consulting normal organic chemistry manuals.

In a first embodiment of the invention, the compound of formula (I) is S-(−)-chlorosuccinic acid ($X_1$ and $X_2$ are hydroxy and Y is chlorine). Said acid can be prepared with good yields and sterospecific reaction, e.g. from L-aspartic acid (S-(+)-aspartic acid) (J. A. Frick, J. B. Klassen, A. Bathe, J. M. Abramson and H. Rapoport, Synthesis, 1992, 7, 621 and literature cited therein), or can be purchased on the market.

In this first embodiment, the reducing agent is diborane.

Carnitine inner salt is then obtained from the reduction product of S-(−)-chlorosuccinic acid, without the isolation of any intermediate product, by treatment with aqueous sodium hydroxide and trimethylamine. The reaction temperature is not critical and can be conveniently selected on the basis of the reaction medium chosen, the reactant concentrations, and all other parameters useful for a successful reaction exploitation. For example, the reaction can be conducted at room temperature, but higher temperatures can also be used compatible with the reaction conditions.

In a second embodiment of the invention, the compound of formula (I) is the one in which $X_1$ is hydroxy, $X_2$ is methoxy, and Y is a halogen, preferably chlorine. This preferred compound can be prepared, for example, starting from S-(−)-chlorosuccinic acid, as seen above, by transformation via the corresponding anhydride. Different 2-halogen-substituted succinic acids are prepared according to known methods.

The conversion is achieved by treating the S-(−)-chlorosuccinic acid with a dehydrating agent, preferably with acetyl chloride/acetic acid or with acetic anhydride, at a temperature ranging from room temperature to 90° C. Other modes of conversion, with other reactants, reaction media and conditions, which the expert technician can deduce from his or her own general knowledge, are also possible. The S-(−)-chlorosuccinic anhydride thus obtained is treated with a suitable amount of methanol to yield the compound of formula (I) desired. Compounds of formula (I) can be obtained, according to variants of this second embodiment of the invention, in which $X_2$ stands for one of the meanings envisaged, alkoxy or phenoxy, using suitable alcohol or phenol in the treatment of the starting anhydride.

In this second embodiment, the reducing agent is a mixed hydride such as lithium borohydride or lithium and aluminium hydride.

Carnitine inner salt is in turn obtained directly from the reduction product of 1-methyl hydrogen (S)-2-chlorosuccinate without the isolation of any intermediate product, with aqueous sodium hydroxide and trimethylanmine, in the same way as described for the first embodiment.

In a third embodiment of the invention, the compound of formula (I) is the one in which $X_1$ and $X_2$ are a halogen, preferably chlorine, and Y is a halogen, preferably chlorine, and, more preferably $X_1$ and $X_2$ and Y are chlorine. S-(−)-chlorosuccinic acid dichloride can be prepared starting from S-(−)-chlorosuccinic acid with known reactions for obtaining acyl chlorides. The other halogen derivatives envisaged in the invention can also be prepared in the same way.

In this third embodiment, the preferred reducing agent is sodium borohydride.

Carnitine inner salt in turn is obtained directly from the reduction product of the previous reaction in exactly the same way as in the cases described above.

In a fourth embodiment of the invention, the compound of formula (I) is the one in which $X_1$ and $X_2$ are hydroxy, and Y is the mesyloxy group. Said compound can be prepared starting from S-malic acid and methanesulphonyl-chloride with known hydroxy acid functionalisation reactions. The compound of formula (I) in which Y is tosyloxy is prepared in the same way.

In this fourth embodiment, the reducing agent is diborane. Carnitine inner salt is then obtained from the reduction product of the previous reaction in exactly the same way as in the cases described above.

In a fifth embodiment of the invention, the compound of formula (I) is the one in which $X_1$ and $X_2$ are methoxy and Y is a halogen, preferably chlorine. Said preferred compound can be prepared as described, for example, in J. Am. Chem. Soc. (1952), 74, 3852–3856, starting from S-(−)-chlorosuccinic acid and diazomethane or with methanol and acid catalysis, preferably in the presence of dehydrating agents.

In this fifth embodiment, the preferred reducing agent is a mixed hydride such as lithium borohydride or lithium and aluminium hydride.

Carnitine inner salt is then obtained from the reduction product of the previous reaction in exactly the same way as in the cases described above.

In a sixth embodiment of the invention, the compound of formula (I) is the one in which $X_1$ and $X_2$ are taken together and are an oxygen atom, and Y is a halogen, or a mesyloxy or a tosyloxy, preferably a halogen. preferably chlorine.

This sixth embodiment shall be described in the foregoing in a particularly detailed manner, being the preferred embodiment, comprising.

the transformation of S-(−)-chlorosuccinic acid into L-carnitine via S-(−)-chlorosuccinic anhydride.

According to this embodiment, the process for the preparation of L-carnitine inner salt includes the following steps:

a) transformation of S-(−)-chlorosuccinic acid into the corresponding S-(−)-chlorosuccinic anhydride;

b) reduction of S-(−)-chlorosuccinic anhydride with a mixed hydride, in the presence of a solvent, obtaining a compound which, without being isolated, is directly converted to L-carnitine inner salt by treatment with an alkaline hydroxide and trimethylamine.

The reaction diagram illustrating this process is the following:

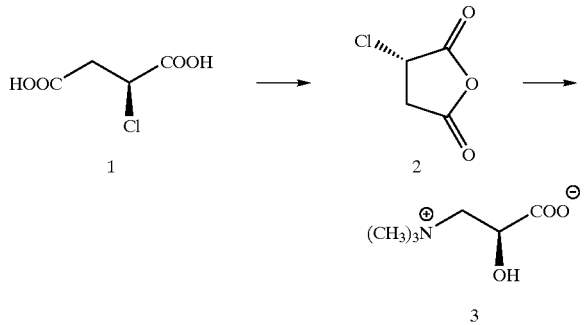

BEST METHOD OF CARRYING OUT THE PROCESS ACCORDING TO THE INVENTION

Preparation of S-(−)-chlorosuccinic Acid

One of the main problems posed in synthesis processes at the industrial level is the ratio of the costs of reactants and materials, such as solvents and auxiliary substances, to the yield of the end product.

In industrial chemistry, increasingly frequent use is being made of chiral compounds, the procuring of which on the market in substantial amounts is adversely affected by the high costs and difficulties in preparation.

S-(−)-chlorosuccinic acid is still by no means easy to procure on the market, suggesting that it may be economically convenient to prepare it within the context of one's own synthesis processes where it is used as an intermediate.

In the reference cited above (J. A. Frick et al., 1992), the preparation of S-(−)-chlorosuccinic acid is simply described as: "S-aspartic acid was converted to S-chlorosuccinic acid by treatment with sodium nitrite in hydrochloric acid". In the diagram on page 621 of the reference cited, the yield of the synthesis step from S-aspartic acid to S-chlorosuccinic acid is 70%. In the experimental part, the only example of preparation is provided for S-bromosuccinic acid, with a yield of 88%. The bromosuccinic acid preparation conditions are not the same as those described for chlorosuccinic acid, though they are taken as an example by analogy. From the industrial point of view, the synthesis of bromosuccinic acid described by Frick et al. is not very convenient in economic terms. In the first place, the dilutions of the reaction mixture are very high; by way of an example, S-(+)-aspartic acid is present to the extent of 5% w/v in the final reaction mixture. A distinct disadvantage arises in the case of isolation of the end product by extraction, which requires a substantial amount of ethyl acetate in order to obtain a 3% w/v solution of S-(−)-bromosuccinic acid. In addition, the end product, obtained with a stoichiometric yield of 88%, is not very pure, particularly as regards optical purity (e.e. =94%).

An improved process has now been found, in the course of development of the invention described herein, for the preparation of S-(−)-chlorosuccinic acid, which makes it possible to achieve an at least 80%, approximately, higher yield, better conditions of reaction, especially in terms of reaction volumes, and of product isolation, and re-use of reactants, with consequent savings in terms of industrial process costs.

Therefore, the framework of the invention described herein covers a process for the preparation of S-(−)-chlorosuccinic acid which includes the reaction between S-(+)-aspartic acid and sodium nitrite in a hydrochloric acid-aqueous milieu, in the presence of sodium chloride, the improvement wherein consists in the isolation of the reaction product by precipitation by means of cooling of the reaction mixture.

Another object of the invention described herein is a process for the preparation of S-(−)-chlorosuccinic acid which includes the reaction between S-(+)-aspartic acid and sodium nitrite in a hydrochloric acid-aqueous milieu, the improvement wherein consists in the use, as a reaction medium, of the mother waters of a previous preparation reaction as in the process described above, said mother waters being used as at least partial substitutes for the sodium chloride and hydrochloric acid envisaged in the first process. According to this second process, the washing waters of the end product of the previous reaction are also used in addition to the mother waters.

The process for the preparation of S-(−)-chlorosuccinic acid according to the invention involves the reaction of S-(+)-aspartic acid-with sodium nitrite, in the presence of sodium chloride and concentrated hydrochloric acid.

The molar ratio of S-(+)-aspartic acid to sodium chloride ranges from 1:0.3 to 1:0.5, preferably from 1:0.35 to 1:0.45. The precipitation is done at a temperature ranging from −10° C. to −20° C., and preferably at −15° C.

According to the invention described herein, the concentration of S-(+)-aspartic acid is greater than 15%, and preferably 16% w/v in the reaction mixture.

In a first embodiment of this process, S-(+)-aspartic acid is suspended in demineralised water in a w/v ratio ranging from 1 kg/L to 0.5 kg/L, preferably 0.66 kg/L, in the presence of sodium chloride, in a molar ratio as described above, and concentrated hydrochloric acid is added in a ratio of S-(+)-aspartic acid to hydrochloric acid ranging from 0.35 kg/L to 0.55 kg/L, preferably 0.45 kg/L. The temperature of the mixture is brought down below 0° C., preferably to −5° C. In a preferred embodiment of the process, the reaction mixture is protected in an inert atmosphere, e.g. nitrogen or argon. Sodium nitrite is then added in portions under stirring in a molar ratio ranging from 1.2 to 2.5, preferably 1.78. The sodium nitrite can be added in solid form or dissolved in a suitable amount of water. When the sodium nitrite is added in the form of a solution, the latter is suitably prepared using part of the water initially envisaged for the aspartic acid suspension. Addition of the sodium nitrite is made by monitoring the reaction temperature.

The reaction progress can be monitored by observing the development of nitrogen. Once the reaction has begun, the development of nitrogen may substitute for the inert atmosphere mentioned above.

To facilitate completion of the reaction, when the addition of sodium nitrite is completed, the reaction temperature can also be raised, either by leaving it to rise spontaneously or by heating the mixture. Preferably, the temperature should be brought up to 0° C.

The isolation of the product is done using conventional methods, but in the context of the invention described herein, it has been found that precipitation of the end product by cooling, e.g. to −15° C., is particularly advantageous, especially as regards the presence of organic impurities in the reaction mixture (unreacted fumaric, malic and aspartic acids).

From the industrial point of view, the process according to the invention is advantageous whether applied in successive cycles or continuously. In fact, successive preparations of S-(−)-chlorosuccinic acid allow part of the reactants to be recovered.

The mother waters and possibly also the washing waters of the first reaction (REACTION A) are used as a reaction medium for a subsequent preparation (REACTION B). Advantageously, the mother waters of REACTION A (in actual fact, a brine) at low temperature (e.g. −15° C.) can be mixed with the other components of the following reaction (REACTION B), which leads to a frigorie saving and to a speeding-up of process times. Advantageously, in REACTION A, the reaction medium also includes the washing waters of REACTION B. In REACTION A, the reaction medium can also include the washing waters of REACTION B.

Thus, another object of the invention described herein is a process for the preparation of S-(−)-chlorosuccinic acid which comprises the reaction between S-(+)-aspartic acid and sodium nitrite in a hydrochloric acid-aqueous milieu, the improvement wherein consists in the use, as a reaction medium, of the mother waters of a previous preparation reaction as described above, said mother waters being used as at least partial substitutes for the sodium chloride and hydrochloric acid envisaged in the first reaction. Preferably, said mother waters are immediately recycled at the S-(−)-chlorosuccinic acid precipitation temperature envisaged for the previous reaction, so that, by mixing them with the reactants still to be added, a temperature for the starting mixture around −5° C., being this latter the normal temperature for this reaction, is immediately available. Advantageously, the washing waters from the previous reaction can also be used in addition to the mother waters.

Alternatively, the process according to the invention includes the reaction between S-(+)-aspartic acid and sodium nitrite in a hydrochloric acid-aqueous milieu, the improvement wherein consists in the use, as a reaction medium, of the mother waters of a previous preparation reaction, said mother waters being used as at least partial substitutes for the sodium chloride and hydrochloric acid envisaged and said S-(−)-chlorosuccinic acid is isolated by extraction. In this case, a yield of over 90% is obtained, without any inorganic residue.

Preferably, said mother waters are immediately recycled at the S-(−)-chlorosuccinic acid precipitation temperature envisaged for the previous reaction, so that, by mixing them with the reactants still to be added, a temperature for the starting mixture around −5° C., being this latter the normal temperature for this reaction, is immediately available. The process according to the invention is even more advantageous if inserted in the context of the process for the preparation of L-carnitine, which is the object of the invention described herein.

In fact, the S-(−)-chlorosuccinic acid, obtained according to the precipitation method described herein contains a percentage of sodium chloride ranging from 15 to 25%, but can be used directly for the preparation of S-(−)-chlorosuccinic anhydride, where the sodium chloride content can be easily eliminated.

Therefore, a further object of the present invention is a process for the preparation of S-(−)-chlorosuccinic anhydride which includes the reaction between S-(−)-chlorosuccinic acid and acetic anhydride, the improvement wherein consists in the use of crude S-(−)-chlorosuccinic acid coming directly from the processes described above.

Preparation of S-(−)-chlorosuccinic Anhydride

S-(−)-chlorosuccinic anhydride, which is obtained from S-(−)-chlorosuccinic acid by converting the bicarboxylic acid into an anhydride, is a new compound and therefore the invention described herein includes said compound as a reaction intermediate in the process described here. The conversion occurs by treating S-(−)-chlorosuccinic acid with a dehydrating agent, preferably acetyl chloride/acetic acid or acetic anhydride, at a temperature ranging from room temperature to 90° C.

The carnitine inner salt is in turn obtained from S-(−)-chlorosuccinic anhydride by reduction with a mixed hydride, preferably $NaBH_4$, in a suitable reaction medium, such as an organic solvent, preferably aprotic, for example, tetrahydrofuran (THF), monoglyme, diglyme, dioxane, ethyl or methyl acetate (EtOAc or MeOAc) or a mixture of the same, and by reaction of the crude product thus obtained with aqueous sodium hydroxide and trimethylamine at temperatures ranging from room temperature to 120° C., preferably from 60° C. to 100° C.

The compounds, 1-methyl hydrogen (S)-2-chlorosuccinate, (S)-2-chlorosuccinoyl dichloride and (S)-methanesulphonyloxysuccinic acid are new and are claimed herein as intermediates for the process according to the invention.

The L-carnitine inner salt can be salified with an acid, as indicated schematically here below:

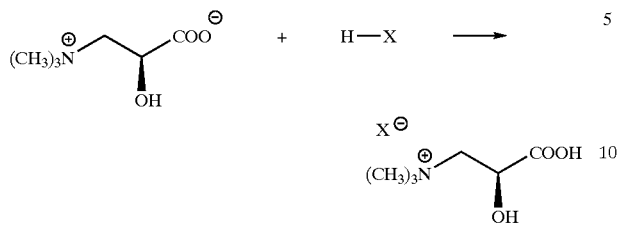

where $X^{\ominus}$ is, for example, a halide ion (preferably chloride), an acid sulphate, a methane sulphonate or an acid fumarate, or

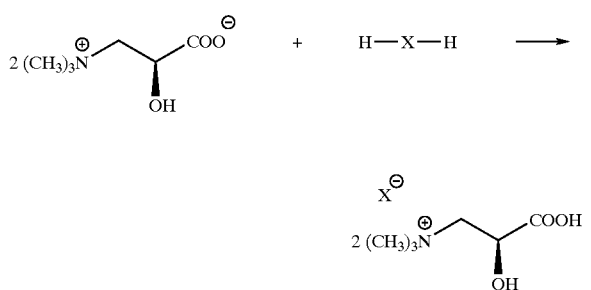

where $X^{2-\ominus}$ is the counter-ion of a bicarboxylic acid, such as, for example, a tartrate ion or a mucate ion.

Of course, all possible salifications with suitable counter-ions are possible, normally counter-ions of non-toxic acids, accepted for pharmaceutical, alimentary and livestock breeding uses, and for the uses envisaged for L-carnitine and its derivatives, e.g. the acyl carnitines, carnitine esters and acyl carnitine esters.

The following examples further illustrate the invention described herein.

EXAMPLE 1

S-(−)-chlorosuccinic Acid "REACTION A"

To a vigorously stirred mixture of 200 g (1.50 mol) of L-aspartic acid, 40 g of sodium chloride (0.68 mol), 440 ml (523.6 g) of 37% HCl (193.74 g of HCl, 5.32 mol), 200 ml of demineralised water, 100 ml of washing waters of the solid obtained in "REACTION B" (see Example 2), are added 184 g (2.66 mol) of solid sodium nitrite in approximately 2 hours at a temperature of −5° C. under nitrogen blanket. Stirring is continued at the same temperature for 2.5 hours, the temperature is raised to +0° C. in the space of approximately 1 hour, the mixture is left at this temperature for another period of 1 hour and then the temperature is lowered to −15° C. After 1.5 hours at that temperature, the mixture is vacuum filtered on Buchner filters and left to "drain" under vacuum pump aspiration for approximately 0.5 hours. The solid is then washed with 80 ml of water at 0° C. and left on a vacuum filter for another 1.5 hours.

The crude product is vacuum dried in an oven at 40° C. It presents approximately 15–20% sodium chloride contamination.

The molar percentages of the impurities present, calculated on the basis of the NMR spectrum, are the following:

| fumaric acid | 0.1–0.2% w/w |
| malic acid | 0.1–0.4% w/w |
| aspartic acid | 0.1–0.2% w/w |

The yield of S-(−)-chlorosuccinic acid, calculated 100% pure, is 80–81%.

EXAMPLE 2

S-(−)-chlorosuccinic Acid "REACTION B"

To a vigorously stirred mixture of mother waters and washing waters (approximately 650 ml) from the previous reaction are added 200 g (1.50 mol) of L-aspartic acid, 360 ml (428.4 g) of 37% HCl (158.51 g of HCl, 4.35 mol) and 100 ml of demineralised water; 184 g (2.66 mol) of solid sodium nitrite are then added in approximately 2 hours at a temperature of −5° C. under nitrogen blanket. Stirring is continued at the same temperature for 2.5 hours, the temperature is raised to +0° C. in the space of approximately 1 hour, the mixture is left at this temperature for another period of 1 hour, and the temperature then lowered to −15° C. After 1.5 hours at this temperature, the mixture is vacuum filtered on Buchner filters and left to "drain" under vacuum pump aspiration for approximately 0.5 hours. The solid is then washed with 80 ml of water at 0° C. and left on a vacuum filter for another 1.5 hours.

The crude product is vacuum dried in an oven at 40° C. It presents approximately 15–20% sodium chloride contamination.

The molar percentages of the impurities present, calculated on the basis of the NMR spectrum, are the following:

| fumaric acid | 0.1–0.2% w/w |
| malic acid | 0.1–0.4% w/w |
| aspartic acid | 0.1–0.2% w/w |

The yield of S-(−)-chlorosuccinic acid, calculated 100% pure, is 86–87%.

The pure product, obtained by means of a further crystallisation of a sample of the crude product with water, has a melting point of 180–182° C.

The overall yield of reactions A(+)B is 83–84%.

EXAMPLE 3

S-(−)-chlorosuccinic Anhydride

A suspension of 300 g (1.97 mol) of S-(−)-chlorosuccinic acid, containing 45–80 g of sodium chloride as a residue of the previous preparation and 241.5 mL (2.56 mol) of acetic anhydride is stirred at 52–55° C. for 3.5 hours. The insoluble sodium chloride is filtered out and the clear, colourless solution is vacuum evaporated and dried. To eliminate the last residues of acetic acid and acetic anhydride, the solid residue is extracted with 300 ml of anhydrous isopropyl ether, the suspension is stirred vigorously for 5 minutes and filtered, and the solid is washed on the filter with another 90 ml (66 g) of fresh isopropyl ether. After vacuum drying in an anhydrous milieu, 251.3 g of S-(−)-chlorosuccinic anhydride are obtained (95%; m.p. 75–80° C.; [α]D=−4.16 (c=1.0; ethyl acetate)).

EXAMPLE 4

S-(−)-chlorosuccinic Anhydride

A suspension of 53 g (0.347 mol) of S-(−)-chlorosuccinic acid in 38 mL (0.40 mol) of acetic anhydride was stirred at 70° C. until the solid was completely dissolved, after which the acetic acid and excess acetic anhydride were vacuum distilled. At this point S-(−)-chlorosuccinic anhydride could be recovered by filtration, after treatment with cyclohexane, or by distillation at 0.5 mm Hg. Yields of around 95% were obtained in all cases (=44.4 g) (ee≧99%).

| Elemental Analysis for: $C_4 H_3 Cl O_3$ | | | |
|---|---|---|---|
| | C % | H % | Cl % |
| Calc. | 35.72 | 2.25 | 26.36 |
| Found | 35.62 | 2.20 | 26.21 |

$[\alpha]_D^{25} = -3.78°$ (c = 10, EtOAc)

$^1$H NMR (CDCl$_3$, δ, p.p.m.): 3.21 (dd, J=18.7), 5.2, (1H, CH$\underline{H}$—CO); 3.59 (dd, J=18.7), 9.0, (1H, CH$\underline{H}$—CO); 4.86 (dd, J=9.0, 5.2, 1H, C$\underline{H}$—Cl);

EXAMPLE 5

1-Methylhydrogen (S)-2-chlorosuccinate

To a solution of 6.00 g (0.0446 mol) of (S)-chlorosuccinic anhydride in 60 mL of CHCl$_3$, without ethanol, held at −65 C, was added slowly a mixture of 1.80 mL (0.0446 mol) of MeOH in 20 mL of CHCl$_3$. The solution was maintained at the same temperature for 1 hour and then left to rise to room temperature in 3 hours. After another 2 hours, the solution was washed with 10 mL of NaOH 1N, dried on anhydrous sodium sulphate and vacuum evaporated to dryness. After purification on a chromatographic column, 5.94 g (80%) of the title compound were obtained. H-NMR in DMSO-d$_6$: δ 2.89 (1H, dd, C$\underline{H}$HCHCl), 3.00 (1H, dd, CHHCHCl), 3.71 (3H, s, COOCH$_3$), 4.78 (1H, t, CHCl).

EXAMPLE 6

(S)-2-chlorosuccinoyldichloride

A suspension of 10.00 g (0.0656 mol) of (S)-chlorosuccinic acid in 20.0 mL (0.274 mol) of thionyl chloride was refluxed for 1 hour. After cooling, the solution was vacuum evaporated to dryness. The residue was distilled at 90–93C/10 mm Hg to obtain 12.56 g (85%) of the title compound. H-NMR in DMSO-d$_6$: δ 3.50 (1H, dd, C$\underline{H}$HCHCl), 3.60 (1H, dd, CH$\underline{H}$CHCl), 5.20 (1H, t, CHCl).

EXAMPLE 7

(S)-methane-sulphonyloxysuccinic Acid

A solution of 8.04 g (0.060 mol) of (S)-malic acid and 9.2 mL (0.120 mol) of methanesulphonyl chloride in 60.0 mL of THF was refluxed for 10 hours. After cooling, the solution was vacuum evaporated to dryness to obtain 12.60 g (99%) of the title compound. H-NMR in DMSO-d$_6$: δ 2.41 (3H, s, CH$_3$SO$_3$), 2.90 (2H, m, CH$_2$), 5.47 (1H, t, CHOSO$_2$).

EXAMPLE 8

Dimethyl (S)-chlorosuccinate

To a solution of 7.04 g (0.046 mol) of (S)-chlorosuccinic acid in 60 mL of methanol were added 2.0 mL of concentrated H$_2$SO$_4$. After 3 days at room temperature the solution was vacuum evaporated and the residue extracted with EtOAc. The solution was washed with a 5% NaHCO$_3$ aqueous solution and the organic phase was dried on Na$_2$SO$_4$. 7.90 g (94%) of the title compound were obtained by evaporation. H-NMR in DMSO-d$_6$: δ 3.00 (1H, dd, C$\underline{H}$HCHCl), 3.12 (1H, dd, CH$\underline{H}$CHCl), 3.61 (3H, s, COOCH$_3$), 3.71 (3H, s, COOCH$_3$), 4.77 (1H, t, CHCl).

EXAMPLE 9

L-carnitine Inner Salt by Reduction of (S)-2-chlorosuccinic Acid

To a suspension of 6.00 g (0.039 mol) of (S)-chlorosuccinic acid in 20 mL of anhydrous THF maintained at −15 C under nitrogen were added 58.5 mL (0.0585 mol) of a 1M solution of borane in THF in 2 hours. After 20 hours at the same temperature, the mixture was treated with 5.5 mL of water and left to stir at room temperature for 3 hours. After the addition of 11 mL of 6M NaOH, the phases were separated. To the aqueous phase were added 7 mL of 40% Me$_3$N in water and the solution was left to stir at room temperature for 3 hours. The solution was vacuum concentrated and the resulting solution brought to pH 5 with 37% HCl. By means of evaporation of this solution a solid was obtained which was extracted with 30 ml of MeOH. The solution obtained by filtration of the insoluble part was vacuum evaporated and dried. The crude product was purified on an ion-exchange column (Amberlite IR 120 form H$^+$) by elution with 2% NH$_4$OH. By means of evaporation of the fractions containing the pure product, 3.14 g (50%) of L-carnitine were obtained.

EXAMPLE 10

L-carnitine Inner Salt by Reduction of 1-methyl hydrogen (S)-2-chlorosuccinate

To a suspension of 6.50 g (0.039 mol) of methyl (S)-2-chlorosuccinate in 30 mL of anhydrous DME held at −15C under nitrogen were added 0.87 g (0.040 mol) of 95% LiBH$_4$ in portions in 2 hours. After 20 hours at the same temperature the mixture was treated as described in Example 9 above to obtain 3.45 g (55%) of L-carnitine.

EXAMPLE 11

L-carnitine Inner Salt by Reduction of (S)-2-chlorosuccinoyl Dichloride

To a solution of 7.39 g (0.039 mol) of (S)-2-chlorosuccinoyl-dichloride in 30 mL of anhydrous DME held at −15C under nitrogen were added 0.74 g (0.0195 mol) of NaBH$_4$ in portions in 2 hours. After 20 hours at the same temperature the mixture was treated as described in example 9 to obtain 2.83 g (45%) of L-carnitine.

EXAMPLE 12

L-carnitine Inner Salt by Reduction of (S)-2-methane-sulphonyloxysuccinic Acid

To a suspension of 8.27 g (0.039 mol) of (S)-methane-sulphonyloxysuccinic acid in 30 mL of anhydrous THF held at −15C under nitrogen were added 58.5 mL (0.0585 mol) of a 1M solution of borane in THF in 2 hours. After 20 hours at the same temperature, the mixture was treated as described in Example 9 to obtain 2.51 g (40%) of L-carnitine.

EXAMPLE 13

L-carnitine Inner Salt by Reduction of dimethyl (S)-2-chlorosuccinate

To a suspension of 7.04 g (0.039 mol) of dimethyl (S)-2-chlorosuccinate in 30 mL of anhydrous DME held at −15C under nitrogen, were added 0.69 g (0.030 mol) of 95% LiBH$_4$ in portions in 2 hours. After 20 hours at the same temperature the mixture was treated as described in Example 9 to obtain 3.32 g (53%) of L-carnitine.

EXAMPLE 14

S-(−)-chlorosuccinic Anhydride

A suspension of 53 g (0.347 mol) of S-(−)-chlorosuccinic acid in 38 mL (0.40 mol) of acetic anhydride was stirred at 70° C. until the solid had completely dissolved, after which the acetic acid and excess acetic anhydride were vacuum distilled. At this point, the S-(−)-chlorosuccinic anhydride could be recovered by filtration after treatment with cyclohexane, or by distillation at 0.5 mm Hg. Yields of around 95% (=44.4 g) were obtained in all cases. (ee≧99%).

| Elemental Analysis for: C$_4$ H$_3$ Cl O$_3$ | | | |
|---|---|---|---|
| | C % | H % | Cl % |
| Calc. | 35.72 | 2.25 | 26.36 |
| Found | 35.62 | 2.20 | 26.21 |

[α]D$^{25}$ = −3.78° (c = 10, EtOAc)

$^1$H NMR (CDCl$_3$, δ, p.p.m.): 4.86 (dd, J=9.0 Hz, 5.2 Hz, 1H, CH-Cl); 3.59 (dd, J=18.7 Hz, 9.0 Hz, 1H, CHH-CO); 3.21 (dd, J=18.7 Hz, 5.2 Hz, 1H, CHH-CO)

L-carnitine Inner Salt

To a vigorously stirred suspension of 6.13 g (0.162 mol) of NaBH$_4$ in 18 mL of anhydrous THF, held at 0° C., were added 43.4 g (0.323 mol) of S-(−)chlorosuccinic anhydride in 90 mL of anhydrous THF. The suspension/solution was stirred for 8 hours at that temperature, then quenched with water, left to stir for one hour and then added with NaOH 4N in two portions, the first to bring the suspension to pH 7.5 and the second, after vacuum evaporating the organic solvent, to ensure total addition of 0.484 mol of NaOH (in all, 121 mL). To said solution were added 51 mL (0.337 mol) of a 40% aqueous solution of Me$_3$N, and the whole was transferred into a closed vessel and held for 16 hours at 70° C. At the end of the reaction, the residual trimethylamine was eliminated by vacuum evaporation and then 80.75 mL (0.323 mol) of HCl 4N were added. The solution, containing L-carnitine inner salt, together with approximately 8% of impurities (mainly fumaric acid, maleic acid, hydroxycrotonic acid, D-carnitine) and sodium chloride, was-desalted by electrodialysis and then vacuum dried. 38.5 g of a crude product were obtained which was crystallised with isobutylic alcohol to yield 31.4 g (60.4%) of pure L-carnitine inner salt. (ee≧99.6%).

| Elemental Analysis for: C$_7$ H$_{15}$ N O$_3$ | | | |
|---|---|---|---|
| | C % | H % | N % |
| Calc. | 52.16 | 9.38 | 8.69 |
| Found | 52.00 | 9.44 | 8.59 |

[α]D$^{25}$ = −31.1° (c = 1.0, H$_2$O)

$^1$H NMR (D$_2$O, δ, p.p.m.): 4.57 (m, 1H, CH-O); 3.41 (d, 2H, CH$_2$-COO); 3.24 (s, 9H, (CH$_3$)$_3$-N); 2.45 (d, 2H, CH$_2$-N)

L-carnitine Chloride

The reaction was repeated exactly as described above, except that, at the end of the reaction in a closed vessel, the contents after cooling were vacuum-dried. The residue was extracted with 53.5 ml (0.646 mol) of 37% HCl and vacuum dried again. The residue was extracted twice with ethanol; the first time with 200 mL and the second time with 60 mL, settling/filtering both times. The pooled ethanol solutions were vacuum-concentrated to a volume of approximately 50 mL, to which were added 600 mL of acetone to precipitate L-carnitine chloride. After one night at room temperature the solid was filtered to yield 47.8 g of crude L-carnitine chloride. 38.5 g (60.4%) of pure L-carnitine chloride were obtained by crystallisation with isopropanol (ee≧99.6%).

| Elemental Analysis for C$_7$ H$_{16}$ Cl N O$_3$ | | | | |
|---|---|---|---|---|
| | C % | H % | Cl % | N % |
| Calc. | 42.54 | 8.16 | 17.94 | 7.09 |
| Found | 42.40 | 8.12 | 18.00 | 7.05 |

[α]D$^{25}$ = −23.0° (c = 0.86, H$_2$O)

$^1$H NMR (CD$_3$OD, δ, p.p.m.): 4.58 (m, 1H, CH-O); 3.48 (m, 2H, CH$_2$-N); 3.27 (s, (CH$_3$)$_3$-N); 2.56 (d, J=6.7 Hz, 2H, CH$_2$-COOH)

What is claimed is:

1. A process for the preparation of S-(−)-chlorosuccinic anhydride comprising
    a) reacting S-(+)-aspartic acid and sodium nitrite in a hydrochloric acid-aqueous milieu in which said S-(+)-aspartic acid suspended in demineralized water in a w/w ratio ranging from 1 kg/L to 0.5 kg/L, and concentrated hydrochloric acid is added in a ratio of S-(+)-aspartic acid to hydrochloric acid ranging from 0.35 kg/L to 0.55 kg/L in the presence of sodium chloride, said S-(+)-aspartic acid and said sodium chloride being in a molar ratio ranging from 1:0.3 to 1:0.5, to give crude S-(−)-chlorosuccinic acid;
    b) isolating said crude S-(−)-chlorosuccinic acid by precipitation by cooling the reaction mixture at a temperature ranging from −10° C. to −20° C.; and
    c) reacting said isolated crude S-(−)-chlorosuccinic acid and acetic anhydride.

* * * * *